(12) United States Patent
Khan et al.

(10) Patent No.: US 11,626,196 B1
(45) Date of Patent: Apr. 11, 2023

(54) CARD-TYPE STORAGE DEVICE WITH DATA UPLOADING FUNCTION AND DATA UPLOADING METHOD APPLIED THERETO

(71) Applicant: Key ASIC Inc., Hsinchu County (TW)

(72) Inventors: Bahadur Shah Khan, Petaling Jaya (MY); Sek Yen Tan, Puchong (MY); Hao-Jen Wu, Hsinchu County (TW)

(73) Assignee: KEY ASIC INC., Hsinchu County (TW)

( * ) Notice: Subject to any disclaimer, the term of this patent is extended or adjusted under 35 U.S.C. 154(b) by 180 days.

(21) Appl. No.: 17/010,868

(22) Filed: Sep. 3, 2020

(30) Foreign Application Priority Data

Jun. 12, 2020 (TW) ................................. 109119923

(51) Int. Cl.
| | | |
|---|---|---|
| *G16H 10/65* | (2018.01) | |
| *G06F 13/38* | (2006.01) | |
| *G06F 13/40* | (2006.01) | |
| *H04L 67/06* | (2022.01) | |
| *G06K 19/077* | (2006.01) | |

(52) U.S. Cl.
CPC ........... *G16H 10/65* (2018.01); *G06F 13/385* (2013.01); *G06F 13/409* (2013.01); *G06F 13/4068* (2013.01); *G06K 19/07732* (2013.01); *G06K 19/07743* (2013.01); *H04L 67/06* (2013.01)

(58) Field of Classification Search
CPC ... G16H 10/65; G06F 13/385; G06F 13/4068; G06F 13/409; G06K 19/07732; G06K 19/07743; H04L 67/06
See application file for complete search history.

(56) References Cited

U.S. PATENT DOCUMENTS

| | | | | |
|---|---|---|---|---|
| 2007/0005829 A1* | 1/2007 | Fujimoto | .............. | G06F 13/385 710/48 |
| 2009/0037647 A1* | 2/2009 | Sugiyama | .............. | G06F 13/385 711/E12.001 |
| 2011/0016267 A1* | 1/2011 | Lee | .......................... | G06F 13/28 710/24 |
| 2011/0273309 A1* | 11/2011 | Zhang | .................... | A61B 5/0013 340/870.07 |
| 2014/0184422 A1 | 7/2014 | Mensinger et al. | | |
| 2014/0320309 A1* | 10/2014 | Zhang | ..................... | G16H 80/00 340/870.07 |
| 2015/0134889 A1* | 5/2015 | Zhong | ...................... | G06F 13/28 710/22 |
| 2015/0199546 A1* | 7/2015 | Sato | .................. | G06K 19/07769 340/10.51 |
| 2020/0341938 A1* | 10/2020 | Nakajima | ................. | G11C 8/18 |
| 2021/0278813 A1* | 9/2021 | Ishikawa | ............... | G05B 19/042 |

* cited by examiner

*Primary Examiner* — Ilwoo Park
*Assistant Examiner* — Aurangzeb Hassan
(74) *Attorney, Agent, or Firm* — WPAT, P.C.

(57) ABSTRACT

A card-type storage device includes a processing chip and a memory module. The processing chip is selectively operated in a data accessing mode or a data uploading mode. The memory module is electrically connected with the processing chip. A first data set generated by the medical device at a first time point and a second data set generated by the medical device at a second time point are stored in the memory module. In the data accessing mode, a first storage list is established by the processing chip according to the first data set, and the first storage list is updated as a second storage list according to the second data set. If the processing chip judges that the second data set satisfies a predetermined condition, the processing chip enters the data uploading mode.

20 Claims, 3 Drawing Sheets

CARD-TYPE STORAGE DEVICE WITH DATA UPLOADING FUNCTION AND DATA UPLOADING METHOD APPLIED THERETO

FIELD OF THE INVENTION

The present invention relates to a card-type storage device with a data uploading function and an associated data uploading method, and more particularly to a card-type storage device and a data uploading method for automatically uploading a data from a medical device to a remote device, so that the data is observed by the user.

BACKGROUND OF THE INVENTION

With the development and progress of medicine, medical technology and medicine, the average life expectancy of modern people is increasing. Consequently, the aging society issues, the long-term care issues or the chronic disease treatment issues become more important.

For example, various real-time medical status monitoring devices (including ventilators) are common medical devices in hospital emergency rooms or intensive care units or even in ordinary households. Take the ventilator for example. If a patient cannot breathe on his own or cannot effectively breathe, the use of the ventilator can maintain life or alleviate the discomfort. Moreover, depending on the situation, condition or category of the patient, the medical personnel can operate the ventilator in an appropriate breathing mode to provide the oxygen supply for the patient. Once the patient begins to use the ventilator for a long time, the burden of the medical personnel on the care work becomes heavier.

When the ventilator is running, relevant data are generated. For example, the data contain the information about minute ventilation, breathing rate, and so on. These data are very important for the medical personnel to set or calculate the appropriate breathing parameters. Consequently, the medical personnel must monitor and make adjustments at any time. If the patient is using the ventilator without medical personnel nearby, or if the medical personnel needs to observe the operation of the ventilator from the remote terminal, other persons may transfer these data to a computer or a mobile phone or connect to the remote terminal through the Internet to transfer the data.

However, the use of the above method to transfer data is very inconvenient. After the data are stored into a general memory card or a USB flash drive and the memory card or the USB flash drive is plugged into a mobile phone or a computer, the data can be read batchwise or further transferred batchwise. The conventional method consumes a lot of work time and is unable to respond to the patient's condition immediately.

SUMMARY OF THE INVENTION

For solving the drawbacks of the conventional technologies, the present invention provides a card-type storage device with a data uploading function and an associated data uploading method for automatically uploading a data from a medical device to a remote device, so that the data is observed by the user. The present invention can effectively facilitate the user or the medical personnel to receive and observe the medical data at the remote terminal. Consequently, the user at the remote terminal can realize the patient's condition in real time.

In accordance with an aspect of the present invention, a data uploading method for a card-type storage device and a medical device is provided. The card-type storage device includes a processing chip and a memory module. The data uploading method includes the following steps. Firstly, the card-type storage device enters a data accessing mode. Then, a first data set is stored into the memory module, and a first storage list is established by the processing chip according to the first data set. The first data set is generated by the medical device at a first time point. Then, a second data set is stored into the memory module, and the first storage list is updated as a second storage list by the processing chip according to the second data set. The second data set is generated by the medical device at a second time point. If the processing chip judges that the second data set satisfies a predetermined condition, the card-type storage device enters a data uploading mode, and associated data of the second data set is uploaded to a back-end host. If the data is uploaded successfully, the card-type storage device is switched from the data uploading mode to the data accessing mode.

In an embodiment, the data uploading method further includes the following steps. If the data is uploaded unsuccessfully, the data from the card-type storage device is continuously uploaded according to a preset upload time duration and/or a preset upload count. If an upload time duration reaches the preset upload time duration and/or an upload count reaches the preset upload count, the data uploading mode of the card-type storage device is switched to the data accessing mode.

In an embodiment, the data uploading method further includes the following steps. If the data is uploaded successfully, an upload status of the data corresponding to the second data set is recorded as an upload complete status. If the data is uploaded unsuccessfully or the processing chip judges that the second data set does not satisfy the predetermined condition, the upload status of the data corresponding to the second data set is recorded as an upload incomplete status.

In an embodiment, the data of the second data set to be uploaded is determined by the processing chip according to an upload status of the second data set, a difference between the second data set and the first data set or a difference between the second storage list and the first storage list.

In an embodiment, the data uploading method further includes the following steps. The predetermined condition is set by a user. If the processing chip judges that the second data set does not satisfy the predetermined condition, the card-type storage device is maintained in the data accessing mode. If a portion or the entire of the data in the second data set are directed to a user-defined storage region of the memory module or a portion or the entire of the data in the second data set are directed to a necessary storage region of the memory module, the second data set satisfies the predetermined condition.

In an embodiment, the card-type storage device further includes a wireless transmission module, and the wireless transmission module is in wireless communication with the back-end host. The data is uploaded by the processing chip through the wireless transmission module.

In an embodiment, the processing chip includes a register unit, and the first storage list is stored in the register unit. When the first storage list is replaced by the second storage list, the second storage list is stored in the register unit.

In an embodiment, the card-type storage device further includes a transmission interface, and the transmission interface is plugged or inserted into the medical device. Consequently, the transmission interface is electrically connected with the medical device.

In an embodiment, the back-end host is a web server, a mobile electronic device, a smart phone, a tablet computer or a computer, and the medical device is a ventilator or a physiological information monitoring device.

In an embodiment, the memory module includes a card slot and a data storage unit. The data storage unit is inserted into the card slot.

In accordance with another aspect of the present invention, a card-type storage device with a data uploading function is provided. The card-type storage device is used with a medical device and a back-end host. The card-type storage device includes a processing chip and a memory module. The processing chip is selectively operated in a data accessing mode or a data uploading mode. The memory module is electrically connected with the processing chip. A first data set generated by the medical device at a first time point and a second data set generated by the medical device at a second time point are stored in the memory module. In the data accessing mode, a first storage list is established by the processing chip according to the first data set, and the first storage list is updated as a second storage list according to the second data set. If the processing chip judges that the second data set satisfies a predetermined condition, the processing chip enters the data uploading mode, and associated data of the second data set is uploaded to the back-end host. If the data is uploaded successfully, the processing chip is switched from the data uploading mode to the data accessing mode.

If the data is uploaded unsuccessfully, the data from the card-type storage device is continuously uploaded according to a preset upload time duration and/or a preset upload count. Moreover, if an upload time duration reaches the preset upload time duration and/or an upload count reaches the preset upload count, the data uploading mode of the card-type storage device is switched to the data accessing mode.

If the data is uploaded successfully, an upload status of the data corresponding to the second data set is recorded as an upload complete status, wherein if the data is uploaded unsuccessfully or the processing chip judges that the second data set does not satisfy the predetermined condition, the upload status of the data corresponding to the second data set is recorded as an upload incomplete status.

In an embodiment, the data of the second data set to be uploaded is determined by the processing chip according to an upload status of the second data set, a difference between the second data set and the first data set or a difference between the second storage list and the first storage list.

In an embodiment, the predetermined condition is set by a user. If the processing chip judges that the second data set does not satisfy the predetermined condition, the card-type storage device is maintained in the data accessing mode. If a portion or the entire of the data in the second data set are directed to a user-defined storage region of the memory module or a portion or the entire of the data in the second data set are directed to a necessary storage region of the memory module, the second data set satisfies the predetermined condition.

In an embodiment, the card-type storage device further includes a wireless transmission module, and the wireless transmission module is in wireless communication with the back-end host, wherein the data is uploaded by the processing chip through the wireless transmission module.

In an embodiment, the processing chip includes a register unit, and the first storage list is stored in the register unit. When the first storage list is replaced by the second storage list, the second storage list is stored in the register unit.

In an embodiment, the card-type storage device further includes a transmission interface, and the transmission interface is plugged or inserted into the medical device. Consequently, the transmission interface is electrically connected with the medical device.

In an embodiment, the back-end host is a web server, a mobile electronic device, a smart phone, a tablet computer or a computer, and the medical device is a ventilator or a physiological information monitoring device.

In an embodiment, the memory module includes a card slot and a data storage unit. The data storage unit is inserted into the card slot.

From the above descriptions, the present invention provides a card-type storage device with a data uploading function and an associated data uploading method. The card-type storage device and the data uploading method of the present invention can effectively facilitate the user or the medical personnel to receive and observe the medical data at the remote terminal. Consequently, it is not necessary for the user to manually acquire the data from the medical device and transfer or return the data. In other words, the technologies of the present invention can help the user or the medical personnel to realize and respond to the patient's condition in real time. As a consequence, the work time is effectively saved, and the safety of patient care is enhanced.

The above objects and advantages of the present invention will become more readily apparent to those ordinarily skilled in the art after reviewing the following detailed description and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for purpose of illustration and description only. In the following embodiments and drawings, the elements irrelevant to the concepts of the present invention are omitted and not shown.

The present invention provides a card-type storage device with a data uploading function and an associated data uploading method. An example will be described as follows.

Figure 1:
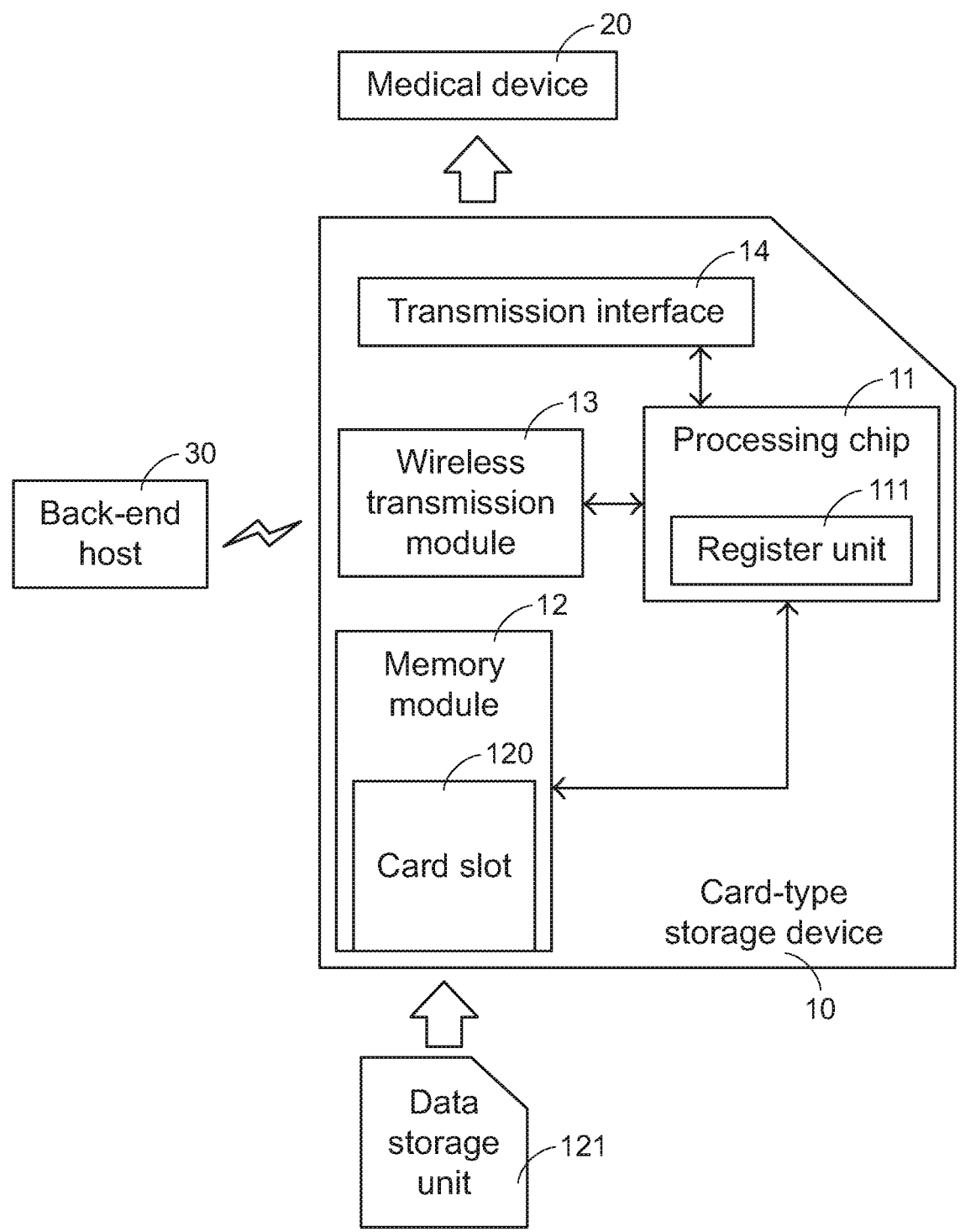
FIG. 1 is a schematic functional block diagram illustrating a card-type storage device according to an embodiment of the present invention.

FIG. 1 is a schematic functional block diagram illustrating a card-type storage device according to an embodiment of the present invention. As shown in FIG. 1, the card-type storage device 10 comprises a processing chip (IC) 11, a memory module 12, a wireless transmission module 13 and a transmission interface 14. The relationships between these components are also shown in FIG. 1.

The hardware structure of the card-type storage device 10 complies with the specification of a secure digital (SD)

memory card. In addition, the card-type storage device 10 can be applied to an electronic device with an interface having a SD-format connecting port or insertion slot. That is, the card-type storage device 10 can be plugged or inserted into the SD-format connecting port or insertion slot.

As shown in FIG. 1, the card-type storage device 10 is used between a medical device 20 and a back-end host 30. In an embodiment, the medical device 20 is a ventilator, and the back-end host 30 is a smart phone. When the card-type storage device 10 is installed in the medical device 20 (i.e., the ventilator), the card-type storage device 10 is electrically connected with the medical device 20 through the transmission interface 14. Consequently, the data can be transmitted between the card-type storage device 10 and the medical device 20.

The examples of the medical device 20 and the back-end host 30 are not restricted. For example, in another embodiment, the medical device 20 is a physiological information monitoring device. That is, the medical device 20 can be used to monitor the physiological information in addition to the breathing condition of the patient. Consequently, the applications are expanded. In some other embodiments, the back-end host 30 is a web server, a mobile electronic device, a tablet computer or a computer. The back-end host 30 is a device for the user or the medical personnel to receive and observe the data at the remote terminal. That is, the wireless transmission method is the principal method of transmitting signals between the card-type storage device 10 and the back-end host 30.

The wireless transmission method is implemented according to the existing communication protocol. For example, the communication protocol includes a fourth generation (4G) protocol, a worldwide interoperability for microwave access (WiMAX) protocol, a radio frequency (RF) protocol, a laser protocol, a Wi-Fi protocol complying with the IEEE 802.11 standard, a Bluetooth protocol, a microwave protocol, an infrared (IR) protocol, a radio frequency identification (RFID) protocol, or a ZigBee protocol complying with the IEEE 802.15.4 protocol. Consequently, the wireless transmission module 13 or the back-end host 30 may be designed according to the practical requirements.

If the remote terminal cannot perform a wireless transmission, the remote terminal may establish a connection with a web server in a wired manner to receive data. Since the ordinary smart phones must use wireless access points to connect to the Internet, the back-end host 30 as shown in FIG. 1 actually establishes a connection with the card-type storage device 10 or the wireless transmission module 13 through a network system.

In the embodiment of FIG. 1, the memory module 12 comprises a card slot 120 and a data storage unit 121. The data storage unit 121 can be inserted into the card slot 120. In an embodiment, the hardware structure of the data storage unit 121 complies with the specification of a Micro SD memory card. Under this circumstance, the card-type storage device 10 is an adapter device, and the data storage unit 121 is a medium for storing data. The data storage unit 121 and the main body of the card-type storage device 10 are fabricated individually.

The applications of the present invention are not restricted. For example, in another embodiment, the memory module is a built-in memory. Since the built-in memory of the memory module has the storing function, the externa data storage unit complying with the specification of the Micro SD memory card may be replaced by the built-in memory of the memory module. Under this circumstance, the card-type storage device 10 is a memory card device rather than the adapter device.

In an embodiment, the data uploading method is executed through a firmware component (not shown) that is installed in the card-type storage device 10. Alternatively, the data uploading method is directly executed by the processing chip 11 through an application program that is stored in a flash memory (e.g., a register unit 111 of the processing chip 11) of the card-type storage device 10. After the card-type storage device 10 is installed in the medical device 20 and electrically connected with the medical device 20, the data uploading method is executed through the firmware component or the application program.

In accordance with a feature of the present invention, the card-type storage device has the data uploading function. The medical device 20 is the well-known medical device. That is, the technologies of the present invention about the card-type storage device and the data uploading method can be applied to the ventilator or any other appropriate medical device that has the function of storing data in the memory card thereof according to the existing technologies. The data uploading method will be described in more details as follows.

Figure 2:
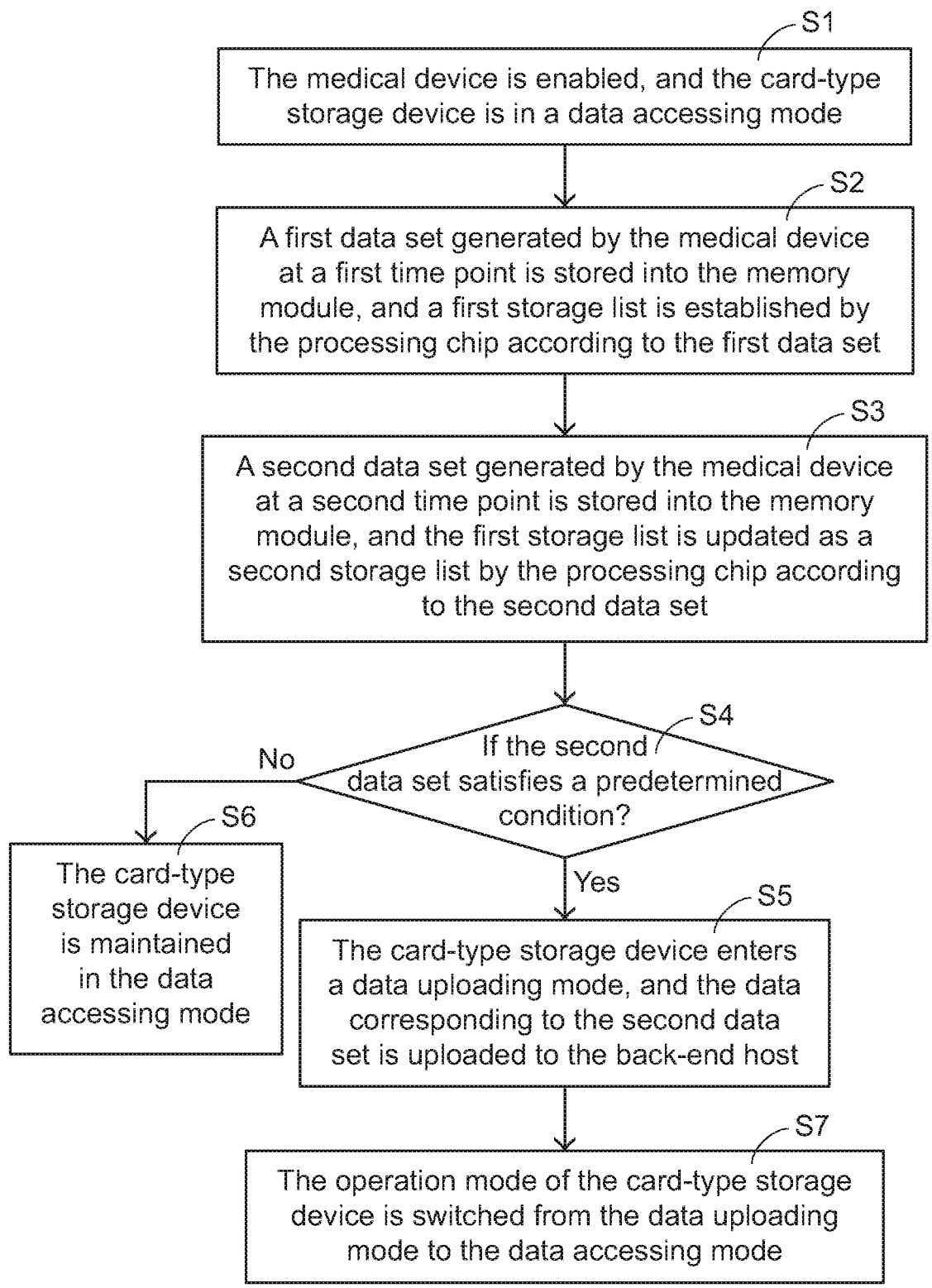
FIG. 2 is a flowchart of a data uploading method according to an embodiment of the present invention.

FIG. 2 is a flowchart of a data uploading method according to an embodiment of the present invention.

Firstly, the medical device 20 is enabled, and the card-type storage device 10 is in a data accessing mode (Step S1). Then, a first data set generated by the medical device 20 at a first time point is stored into the memory module 12, and a first storage list is established by the processing chip 11 according to the first data set (Step S2). Then, a second data set generated by the medical device 20 at a second time point is stored into the memory module 12, and the first storage list is updated as a second storage list by the processing chip 11 according to the second data set (Step S3). Then, the processing chip 11 judges whether the second data set satisfies a predetermined condition (Step S4). If the processing chip 11 judges that the second data set satisfies the predetermined condition, the card-type storage device 10 enters a data uploading mode, and the data corresponding to the second data set is uploaded to the back-end host 30 (Step S5). Whereas, if the processing chip 11 judges that the second data set does not satisfy the predetermined condition, the card-type storage device 10 is maintained in the data accessing mode (Step S6). If the data is uploaded successfully after the step S5, the operation mode of the card-type storage device 10 is switched from the data uploading mode to the data accessing mode (Step S7).

In the step S1, the medical device 20 (e.g., the ventilator) is enabled. Consequently, the operating data (e.g., minute ventilation, breathing rate or associated information) is continuously generated. Since the card-type storage device 10 has been installed in the medical device 20, the card-type storage device 10 and the medical device 20 can transmit data. In other words, the card-type storage device 10 is in the data accessing mode in the step S1. Consequently, the medical device 20 can output data to the card-type storage device 10, and the data from the medical device 20 can be stored into the card-type storage device 10.

In the step S2, the first time point denotes an early time point. That is, the first data set contains one or more older data. The step S1 and S2 are defined as an initial standard at the beginning of the data uploading method. In the step S1 and S2, the data in the first data set may have been uploaded or not been uploaded according to the practical requirements. In this stage, it is not described whether the data have been uploaded or not been loaded. Whereas, the first data set is used as a comparison object with respect to the generated new data in the subsequent step.

The first storage list records the currently-stored data (i.e., the first data set). In addition to the file names of the data, the generation time points of the data, the upload statuses of the data (i.e., the information about the result of judging whether the data have been uploaded or not been uploaded) or any other appropriate information are recorded in the first storage list.

In an embodiment, the first storage list is stored in the register unit 111 of the processing chip 11. When the data uploading function of the present invention is enabled, the processing chip 11 reads the data from the register unit 111 in real time. After the data are recognized, the processing chip 11 makes further judgment.

In the step S3, the second time point denotes a later time point. That is, the second time point is a time point posterior to the first time point, and the second data set contains one or more newer data with respect to the first data set. For example, the second data set contains the data that are newly generated by the medical device 20 (e.g., the ventilator). Since the data stored in the memory module 12 have been changed at this moment, the first storage list is updated as the second storage list by the processing chip 11 according to this data change.

If the first data set is still stored in the memory module 12 and the second data set is newly added and stored in the memory module 12 with respect to the first data set, the contents of the second storage list are directed to the entire of the first data set and the entire of the second data set. Whereas, if the second data set stored in the memory module 12 replaces a portion of the first data set, or a portion of the first data set are deleted and the new data are added (e.g., in an overwrite update method), the contents of the second storage list are directed to the remaining portion of the first data set and the newly-added second data set.

Similarly, the second storage list is also stored in the register unit 111. Since the first storage list is replaced by or updated as the second storage list, the first storage list has been discarded. Moreover, the contents of the second storage list contain the file names of all data stored in this stage, the generation time points of the data, the upload statuses of the data (i.e., the information about the result of judging whether the data have been uploaded or not been uploaded) or any other appropriate information. Since the new data have not been uploaded in the step S3, the upload status in the second storage list indicates that the data have not been uploaded, no record is present, or the event is pending.

In the step S4, the predetermined condition is previously set by the user. For example, the predetermined condition is set by the medical personnel who operates the medical device 20 (e.g., the ventilator), or the predetermined condition is set by the medical personnel who operates the back-end host 30 (e.g., the smart phone). For example, the user may download the associated application program to the back-end host 30 (e.g., the smart phone). When the application program is executed, an interface for allowing the user to remotely observing the data of the medical device is provided and a user operation interface is shown for allowing the user to make selection.

In the step S4, the processing chip 11 judges whether the second data set satisfies the predetermined condition. Consequently, the predetermined condition may be specially set according to the second data set. In an embodiment, the second data set satisfies the predetermined condition when a portion or the entire of the data in the second data set are directed to a user-defined storage region of the memory module 12 (see FIG. 3A). Alternatively, the second data set satisfies the predetermined condition when a portion or the entire of the data in the second data set are directed to a necessary storage region of the memory module 12 (see FIG. 3B). Especially, the user can select the concerned storage items in the memory module 12. Since the data generated by the medical device 20 contain the important information such as the minute ventilation or the breathing rate, the important data will be selected by the user compulsively through the setting of the application program.

Figure 3A:
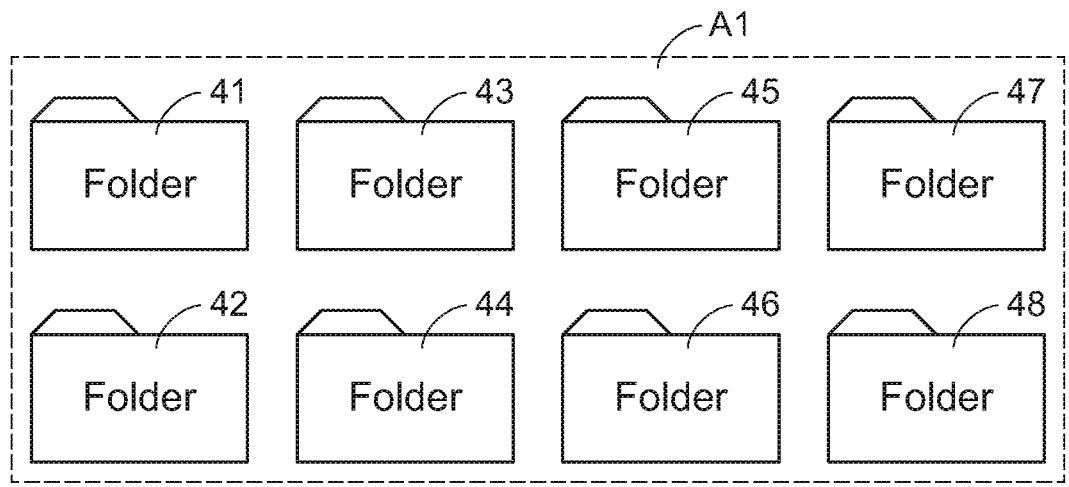
FIGS. 3A and 3B schematically illustrate two methods of defining the storage region in the memory module according to the predetermined condition.
Figure 3B:
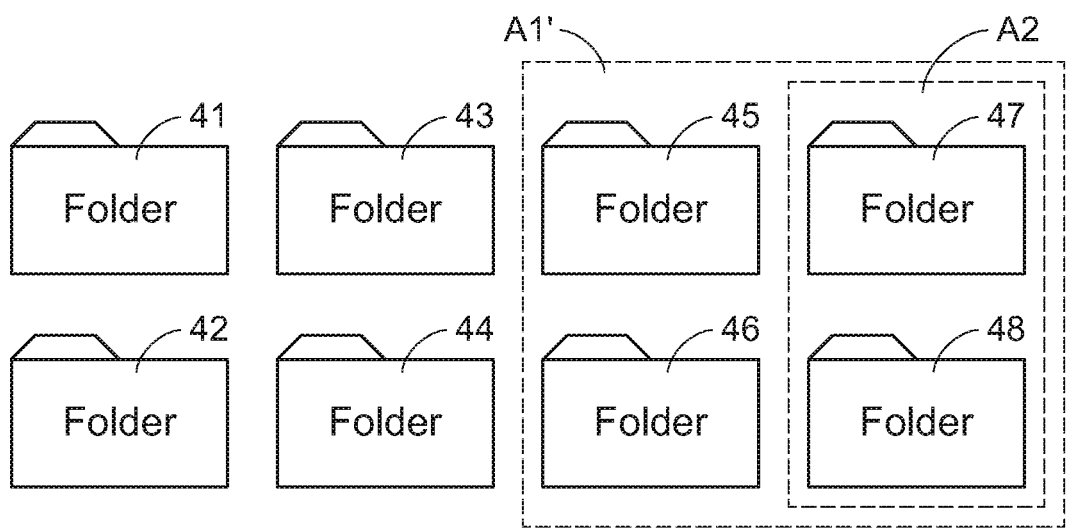

FIGS. 3A and 3B schematically illustrate two methods of defining the storage region in the memory module according to the predetermined condition. As shown in FIGS. 3A and 3B, data can be stored in plural folders (e.g., the folders 41~48) of the memory module 12. Moreover, different output items from the medical device 20 may be stored in different folders. In an embodiment, the folder may store older data and new data simultaneously.

In the example of FIG. 3A, the user-defined storage region A1 includes the folders 41~48. That is, whenever a new data (e.g., the second data set) is generated, all output items need to be further judged. In the example of FIG. 3B, the user-defined storage region A1' includes the folders 45~48. That is, whenever a new data (e.g., the second data set) is generated, only the data in the user-defined storage region A1' (e.g., a portion or the entire of the second data set) need to be judged.

As shown in FIG. 3B, the user-defined storage region A1' further contains a necessary storage region A2. That is, even if not all of the items or the folders are concerned and selected, the important data are not missed. In an embodiment, the items to be compulsively selected by the user through the user operation interface of the application program are included in the necessary storage region A2.

It is noted that the way of setting the predetermined condition or the way of storing the data is not restricted. Moreover, as the amount of the data to be selected and judged increases, the time period of processing the data is extended. Consequently, in the step S4, the processing chip 11 judges whether there are data complying with the user's requirements according to the predetermined condition.

As mentioned above, the important data need to be selected compulsively. However, if the data generated at a certain time point do not contain the important data (even though this situation may be rare) and the data are not the user-defined concerned items, the predetermined condition is not satisfied. Under this circumstance, the step S6 is performed. That is, the card-type storage device 10 is maintained in the data accessing mode under control of the processing chip 11.

If the processing chip 11 judges that the second data set satisfies the predetermined condition, the step S5 is performed. That is, the operation mode of the card-type storage device 10 is switched from the data accessing mode to the data uploading mode under control of the processing chip 11. In an embodiment, a portion or the entire of the data in the second data set are uploaded in the data uploading mode. The data of the second data set to be uploaded may be determined by the processing chip 11 according to the upload status of the second data set, the difference between the second data set and the first data set or the difference between the second storage list and the first storage list.

For example, the second data set containing the newer data is not uploaded in this stage. That is, the upload status indicates that the data have not been uploaded. If the data in the second data set are directed to the user-defined concerned items or important data, the data are arranged to be uploaded. Alternatively, the newly-added second data set is directly uploaded because the data in the second data set are newer than the data in the first data set or the second data set is stored in an overwrite update method (i.e., added after deleted). Alternatively, the difference between the second storage list and the first storage list is recorded when the first storage list is updated. According to the result of comparing the second storage list with the first storage list, the processing chip 11 can determine the data to be uploaded.

When the card-type storage device 10 is in the data uploading mode, the data to be uploaded from the memory module 12 to the back-end host 30 are being processed by the processing chip 11 and the wireless transmission module 13. Meanwhile, the data transmission between the transmission interface 14 and the medical device 20 cannot be performed. That is, the data storing procedure and the data uploading procedure are not simultaneously performed. Even if new data are generated by the medical device 20 at this moment, the new data are not transmitted to the card-type storage device 10 for storage. After the data uploading procedure is completed and the operation mode is switched to the data accessing mode, the new data can be transmitted to the card-type storage device 10 for storage. The mechanism of switching the operation mode between the data accessing mode and the data uploading mode is controlled by the processing chip 11.

After the corresponding data are transmitted to the back-end host 30 in the data uploading mode, the step S7 is performed. Since the operation mode is switched from the data uploading mode to the data accessing mode by the processing chip 11, the card-type storage device 10 can receive the new data from the medical device 20 continuously. Moreover, after the corresponding data in the second data set have been uploaded successfully, the data uploading method further comprises a step of recording the upload status of these data as "Upload complete".

In some situations, the data cannot be uploaded normally. For example, if the network connection fails because of the network problem or the hardware problem during the data uploading process, the data are uploaded unsuccessfully. After the processing chip 11 judges that the corresponding data in the second data set are uploaded unsuccessfully, the data uploading method further comprises a step of recording the upload status of these data as "Upload incomplete".

As mentioned above, if the processing chip 11 judges that the second data set does not satisfy the predetermined condition in the step S4, the card-type storage device 10 is maintained in the data accessing mode (Step S6). In other words, the associated data are not stored in the user-defined storage region (e.g., the storage region A1' as shown in FIG. 3B) or the necessary storage region (e.g., the storage region A2 as shown in FIG. 3B), but these data are not the user-defined concerned items or the important data (e.g., the folders 41~44 as shown in FIG. 3B). Consequently, these data will not be uploaded. Similarly, the data uploading method further comprises a step of recording the upload status of these data as "Upload incomplete".

As mentioned above, the data uploading method of the present invention further comprises a step of recording the upload status of the corresponding data of the second data set. Regardless of whether the upload status of the corresponding data is recorded as "Upload incomplete" or "Upload complete", the contents of the second storage list is modified and updated. That is, the upload statuses of the data corresponding to the second storage list in the register unit 111 are originally recorded as "Upload incomplete", "No record" or "Pending". After the data uploading procedure, the records about these upload statuses have been changed. Consequently, the contents of the second storage list have been changed. In other words, it is considered that the second storage list is updated as a third storage list in this stage.

It is noted that the data uploading method of the present invention may be further modified. For example, after the processing chip 11 judges that the data are uploaded unsuccessfully or abnormally, the data uploading method further comprises an extending judgment step for reuploading the data after the step S5. The extending judgment step includes the following steps. If the data are uploaded unsuccessfully, the card-type storage device 10 continuously uploads the data according to a preset upload time duration and/or a preset upload count. If an upload time duration reaches the preset upload time duration and/or an upload count reaches the preset upload count, the data uploading mode of the card-type storage device 10 is ended, and the operation mode is switched to the data accessing mode.

As mentioned above, the data reuploading procedure is performed when the processing chip 11 judges that the data are uploaded unsuccessfully or abnormally. Moreover, the timing of ending the data reuploading procedure is determined according to the preset upload time duration and/or the preset upload count. That is, if the preset upload time duration and/or the preset upload count is not reached, the card-type storage device 10 performs the data reuploading procedure. That is, the step S5 is continuously performed until the data are uploaded successfully. If the data are still uploaded unsuccessfully when the preset upload time duration and/or the preset upload count is reached, the data reuploading procedure is ended. Similarly, after the data reuploading procedure is performed and the processing chip 11 confirms that the data have been uploaded successfully or the data are uploaded unsuccessfully, the records about the upload statuses of the data are modified and updated.

In some embodiments, the old data that are uploaded unsuccessfully in the previous time will be reuploaded when the operation mode is switched again. For example, whenever new data are ready to be uploaded, the processing chip 11 checks the records about the upload statuses of the old data. If the upload status indicates that the old data has not been uploaded, the old data and the new data will be uploaded together.

Moreover, the data uploading method may be automatically executed, or the data uploading function may be automatically enabled. After the card-type storage device 10 is installed in the medical device 20 and the medical device 20 is enabled, the firmware component using the data uploading method or the application program in the corresponding memory unit is automatically executed. Since the data from the medical device 20 are generated continuously, the operation mode of the card-type storage device 10 is continuously switched between the data accessing mode and the data uploading mode under control of the processing chip 11 while the data uploading method is executed. That is, the steps S1~S7 of the flowchart as shown in FIG. 2 are repeatedly done.

It is noted that numerous modifications and alterations may be made while retaining the teachings of the invention.

Generally, if the operation mode is frequently switched between the data accessing mode and the data uploading mode, the power consumption will increase and the overall performance will deteriorate. In addition, whenever the data are updated, it is usually not necessary to upload the data immediately. For reducing the frequency of switching the operation mode, the data uploading method may further comprise a step of providing a data priority judgment mechanism in order to determine the suitable timing of switching the operation mode. This purpose may be achieved through the necessary storage region or the user-defined concerned items. Alternatively, in another embodiment, the operation mode is switched to the data uploading mode and the data are uploaded when the accumulated amount of new data reaches a specified amount.

From the above descriptions, the present invention provides a card-type storage device with a data uploading function and an associated data uploading method. The card-type storage device and the data uploading method of the present invention can effectively facilitate the user or the medical personnel to receive and observe the medical data at the remote terminal. Consequently, it is not necessary for the user to manually acquire the data from the medical device and transfer or return the data. In other words, the technologies of the present invention can help the user or the medical personnel to realize and respond to the patient's condition in real time. As a consequence, the work time is effectively saved, and the safety of patient care is enhanced.

In other words, the technologies of the present invention can overcome the drawbacks of the conventional technologies while achieving the objects of the present invention While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all modifications and similar structures.

What is claimed is:

1. A data uploading method for a card-type storage device and a medical device, the card-type storage device comprising a processing chip, a memory module and a wireless transmission module, the data uploading method comprising steps of:
   allowing the card-type storage device to enter a data accessing mode;
   storing a first data set into the memory module, and establishing a first storage list by the processing chip according to the first data set, wherein the first data set is generated by the medical device at a first time point;
   storing a second data set into the memory module, and updating the first storage list as a second storage list by the processing chip according to the second data set, wherein the second data set is generated by the medical device at a second time point;
   if the processing chip judges that the second data set satisfies a predetermined condition, allowing the card-type storage device to enter a data uploading mode, and uploading associated data of the second data set to a back-end host; and
   if the associated data is uploaded successfully, switching the card-type storage device from the data uploading mode to the data accessing mode;
   wherein the medical device is a ventilator or a physiological information monitoring device, the card-type storage device is a memory card plugged or inserted into the medical device, and wherein the data accessing mode and the data uploading mode are not simultaneously performed.

2. The data uploading method according to claim 1, wherein the data uploading method further comprises steps of:
   if the associated data is uploaded unsuccessfully, continuously uploading the associated data from the card-type storage device according to a preset upload time duration and/or a preset upload count; and
   if an upload time duration reaches the preset upload time duration and/or an upload count reaches the preset upload count, switching the data uploading mode of the card-type storage device to the data accessing mode.

3. The data uploading method according to claim 1, wherein the data uploading method further comprises steps of:
   if the associated data is uploaded successfully, recording an upload status of the associated data corresponding to the second data set as an upload complete status; and
   if the associated data is uploaded unsuccessfully or the processing chip judges that the second data set does not satisfy the predetermined condition, recording the upload status of the associated data corresponding to the second data set as an upload incomplete status.

4. The data uploading method according to claim 1, wherein the associated data of the second data set to be uploaded is determined by the processing chip according to an upload status of the second data set, a difference between the second data set and the first data set or a difference between the second storage list and the first storage list.

5. The data uploading method according to claim 1, wherein the data uploading method further comprises steps of:
   setting the predetermined condition by a user; and
   if the processing chip judges that the second data set does not satisfy the predetermined condition, maintaining the card-type storage device in the data accessing mode,
   wherein if a portion or the entire of the data in the second data set are directed to a user-defined storage region of the memory module or a portion or the entire of the data in the second data set are directed to a necessary storage region of the memory module, the second data set satisfies the predetermined condition.

6. The data uploading method according to claim 1, wherein the wireless transmission module is in wireless communication with the back-end host, wherein the associated data is uploaded by the processing chip through the wireless transmission module.

7. The data uploading method according to claim 1, wherein the processing chip comprises a register unit, and the first storage list is stored in the register unit, wherein when the first storage list is replaced by the second storage list, the second storage list is stored in the register unit.

8. The data uploading method according to claim 1, wherein the card-type storage device further comprises a transmission interface, and the transmission interface is plugged or inserted into the medical device, so that the transmission interface is electrically connected with the medical device.

9. The data uploading method according to claim 1, wherein the back-end host is a web server, a mobile electronic device, a smart phone, a tablet computer or a computer.

10. The data uploading method according to claim 1, wherein the memory module comprises a card slot and a data storage unit, wherein the data storage unit is inserted into the card slot.

11. A card-type storage device with a data uploading function, the card-type storage device being used with a medical device and a back-end host, the card-type storage device comprising:

a wireless transmission module;
a processing chip selectively operated in a data accessing mode or a data uploading mode; and
a memory module electrically connected with the processing chip, wherein a first data set generated by the medical device at a first time point and a second data set generated by the medical device at a second time point are stored in the memory module,
wherein in the data accessing mode, a first storage list is established by the processing chip according to the first data set, and the first storage list is updated as a second storage list according to the second data set,
wherein if the processing chip judges that the second data set satisfies a predetermined condition, the processing chip enters the data uploading mode, and associated data of the second data set is uploaded to the back-end host,
wherein if the associated data is uploaded successfully, the processing chip is switched from the data uploading mode to the data accessing mode;
wherein the medical device is a ventilator or a physiological information monitoring device, the card-type storage device is a memory card plugged or inserted into the medical device, and wherein the data accessing mode and the data uploading mode are not simultaneously performed.

12. The card-type storage device according to claim 11, wherein if the associated data is uploaded unsuccessfully, the data from the card-type storage device is continuously uploaded according to a preset upload time duration and/or a preset upload count, wherein if an upload time duration reaches the preset upload time duration and/or an upload count reaches the preset upload count, the data uploading mode of the card-type storage device is switched to the data accessing mode.

13. The card-type storage device according to claim 11, wherein if the associated data is uploaded successfully, an upload status of the associated data corresponding to the second data set is recorded as an upload complete status, wherein if the associated data is uploaded unsuccessfully or the processing chip judges that the second data set does not satisfy the predetermined condition, the upload status of the associated data corresponding to the second data set is recorded as an upload incomplete status.

14. The card-type storage device according to claim 11, wherein the associated data of the second data set to be uploaded is determined by the processing chip according to an upload status of the second data set, a difference between the second data set and the first data set or a difference between the second storage list and the first storage list.

15. The card-type storage device according to claim 11, wherein the predetermined condition is set by a user, wherein if the processing chip judges that the second data set does not satisfy the predetermined condition, the card-type storage device is maintained in the data accessing mode, wherein if a portion or the entire of the data in the second data set are directed to a user-defined storage region of the memory module or a portion or the entire of the data in the second data set are directed to a necessary storage region of the memory module, the second data set satisfies the predetermined condition.

16. The card-type storage device according to claim 11, wherein the wireless transmission module is in wireless communication with the back-end host, wherein the associated data is uploaded by the processing chip through the wireless transmission module.

17. The card-type storage device according to claim 11, wherein the processing chip comprises a register unit, and the first storage list is stored in the register unit, wherein when the first storage list is replaced by the second storage list, the second storage list is stored in the register unit.

18. The card-type storage device according to claim 11, wherein the card-type storage device further comprises a transmission interface, and the transmission interface is plugged or inserted into the medical device, so that the transmission interface is electrically connected with the medical device.

19. The card-type storage device according to claim 11, wherein the back-end host is a web server, a mobile electronic device, a smart phone, a tablet computer or a computer.

20. The card-type storage device according to claim 11, wherein the memory module comprises a card slot and a data storage unit, wherein the data storage unit is inserted into the card slot.

* * * * *